US008512976B2

(12) United States Patent
Druggan (10) Patent No.: US 8,512,976 B2
(45) Date of Patent: *Aug. 20, 2013

(54) SELECTIVE GROWTH MEDIA (75) Inventor: Patrick Druggan, Basingstoke (GB)

(73) Assignee: Oxoid Limited (GB)

(*) Notice: Subject to any disclaimer, the term of this patent is extended or adjusted under 35 U.S.C. 154(b) by 440 days.

This patent is subject to a terminal disclaimer.

(21) Appl. No.: 12/762,765

(22) Filed: Apr. 19, 2010

(65) Prior Publication Data

US 2010/0248331 A1 Sep. 30, 2010

Related U.S. Application Data (63) Continuation of application No. 10/380,330, filed as application No. PCT/GB01/04124 on Sep. 14, 2001, now Pat. No. 7,704,706.

(30) Foreign Application Priority Data

Sep. 14, 2000 (GB) ................................. 0022556.5

(51) Int. Cl.
*C12Q 1/04* (2006.01)
(52) U.S. Cl.
USPC ............................................................ 435/34
(58) Field of Classification Search
None
See application file for complete search history.

(56) References Cited

U.S. PATENT DOCUMENTS

| | | | |
|---|---|---|---|
| 4,016,148 A | 4/1977 | Atherton et al. |
| 4,128,542 A | 12/1978 | Atherton et al. |
| 4,134,972 A | 1/1979 | Atherton et al. |
| 4,923,965 A | 5/1990 | Andruszkiewicz et al. |
| 5,658,747 A | 8/1997 | Feldsine et al. |
| 5,843,699 A | 12/1998 | Strenkoski et al. |

FOREIGN PATENT DOCUMENTS

| | | |
|---|---|---|
| WO | WO-89/04839 A1 | 6/1989 |
| WO | WO9902650 A1 | 1/1999 |
| WO | WO-02/24725 A1 | 3/2002 |

OTHER PUBLICATIONS

International Search Report for International Application No. PCT/GB01/04144 (3 pages).
Richard I. Tomlins, et al., "Requirements of Salmonella typhimurium for Recovery from Thermal Injury", Journal of Bacteriology, Feb. 1971, pp. 512-518, vol. 105, No. 2, 1969, American Society for Microbology, USA.
Carol W. Clark, et al., "Thermal Injury and Recovery of Salmonella typhimurium and Its Effect on Enumeration Procedures", Applied Microbiology, Sep. 1969, pp. 332-336, vol. 18, No. 3, 1969, American Society for Microbiology, USA.
J. Y. D'Aoust, "Recovery of Sublethally Heat-Injured Salmonella typhimurium on Supplemented Plating Media", Applied and Environmental Microbiology, Mar. 1978, pp. 483-486, vol. 35, No. 3, 1978, American Society for Microbiology, USA.
D.L. Scheusner, et al., "Inhibition of Injured *Escherichia coli* by Several Selective Agents", Applied Microbiology, Jan. 1971, pp. 46-49, vol. 21, No. 1, 1971, American Society for Microbiology, USA.
R. Reissbrodt, et al., "Resuscitation of Salmonella enterica erovar Tyhpimurium and Enterohemorrgic *Escherichia coli* from the Viable but Nonculturable Sate by Heat-Stable Enterobacterial Autoinducer", Applied and Environmental Microbiology, Oct. 2002, pp. 4788-4794, vol. 68, No. 10, 2002, American Society for Microbiology.
P.J. Stephens, et al., "Recovery of Stressed Microorganisms", Culture Media for Food Microbioligy, J.E.L. Corry et al. (Eds.), 2002 Elsevier Science B.V., pp. 25-48.
Pieter A. Gouws, et al., "A Polymerase Chain Reaction Procedure for the Detection of Salmonella spp. within 24 Hours", Journal of Food Protection, vol. 61, No. 8, 1988, pp. 1039-1042, International Association of Milk, Food and Environmental Sanitarians.
C.E. Park et al., "Selective Enrichment of Shigella in the presence of *Escherichia coli* by use of 4-chloro-2-cyclopentylphenyl B-D-Galactopyranoside", Can. J. Microbiol, 1976, 22(5), pp. 654-657.
J.G. Allen et al, "Phosphono peptides as Anti-bacterial Agents, Alaphosphin and Related Phosphono peptides", Antimicrobial Agents and Chemotherapy, 1979 vol. 15, No. 5, pp. 684-695.
Webster's Online Dictionary, "Shigella" http://www.webster-dictionary.org/definition/shigella accessed Dec. 20, 2004.
Webster's Online Dictionary, "*E.coli*" http://www.webster-dictionary.org/definition/e.%20coli accessed Dec. 20, 2004.
Webster's Online Dictionary, "Salmonella" http://www.webstersdictionary.org/definition/salmonella accessed Dec. 21, 2004.
Johnson et al, "Selective Inhibition of *Escherichia coli* in the presence of Salmonella typhimurium by Phenethyl B-D-Galactopyranoside" Applied Microbiol, 1967, vol. 15, No. 5, pp. 1223-1228.
Allen et al, "Phosphonopeptides, a new class of synthetic antibacterial agents," Nature, 1978, vol. 272, pp. 56-58.
Milewski et al, "Synthetic derivatives of N3-fumaroyl-L-2,3-diaminopropanoic acid inactivate glucosamine synthetase from Candida albicans" 1985, vol. 828, pp. 247-254.
Atherton et al, "Phosphonopeptides as Antibacterial Agents: Rationale, Chemistry, and Structure-Activity Relationships" 1979, Antimicrob. Agents Chemother., vol. 15, No. 5, pp. 677-683.
North Jr, WR "Lactose Pre-enrichment method for isolation of Salmonella from dried-egg albumin: Its use in a survey of commerically produced albumin" Applied Microbiology, 1961, vol. 9, No. 3, pp. 188-195.

*Primary Examiner* — Suzanne M Noakes
*Assistant Examiner* — Stephen Chong
(74) *Attorney, Agent, or Firm* — Rader, Fishman & Grauer PLLC

(57) ABSTRACT

Disclosed is a method of selectively inhibiting for growth of non-target cells in a mixed population of target and non-target cells, the method comprising the steps of: (a) contacting the mixed population with a selective agent which comprises a carrier moiety linked by a scissile linkage to a toxic moiety; wherein the selective agent is able to enter non-target cells in which the scissile linkage is cleaved, releasing the toxic moiety to exert a toxic effect on the non-target cells causing inhibition of the growth of the non-target cells, whereas the selective agent is unable to enter target cells and/or the scissile linkage is not cleaved in target cells and/or toxic moiety, if released from the selective agent, does not exert a toxic effect on the target cell; and (b) culturing the cells in conditions which allow for growth of non-inhibited cells.

3 Claims, 11 Drawing Sheets

*Fig. 1A*

*Fig. 1B* aminopeptidase

*Fig. 1C*

L-amino acid

*Fig. 15* total viable count of *Klebsiella pneumoniae* grown in Nutrient Broth

L-pyroglutamyl-L-1-aminoethylphosphonic acid

*Fig. 21*

SELECTIVE GROWTH MEDIA

CROSS REFERENCE TO RELATED APPLICATIONS

This application is a continuation application and claims priority to U.S. Ser. No. 10/380,330 filed on Sep. 12, 2003, which is a National Phase Patent Application of PCT/GB01/04124 filed on Sep. 14, 2001, which claims benefit of Great Britain Patent Application No. 0022556.5 filed on Sep. 14, 2000, each of said applications being hereby incorporated by reference in their entireties.

FIELD OF THE INVENTION

This invention relates to a method of selectively inhibiting the growth of certain cells in a mixed population, a selective medium for use in the method, and a kit for performing the method.

BACKGROUND OF THE INVENTION

Many selective agents are known which, when incorporated into biological growth media, allow for the preferential growth (i.e. selection) of particular organisms, especially particular bacteria. It is well-known, for example when performing a bacterial transformation, to incorporate an antibiotic resistance gene on the transforming DNA, and subsequently exposing the mixed population of transformed and untransformed cells to the relevant antibiotic, thereby inhibiting the growth of untransformed cells and selecting for transformed cells.

Equally, it is known to use various dye substances or salts to select for a particular organism (e.g. a pathogen) in a mixed population of bacteria present in a sample obtained from a human or animal subject, as an aid to diagnosis of infectious diseases. However, these selective agents are known to inhibit the growth of healthy cells (Vassiliadis et al, 1974 J. Appl. Bacteriol. 37, 411-418) and to restrict the recovery of injured cells (Kang & Siragusa 1999 Appl. and Env. Microbiol. 65, 5334-5337). This is a severe disadvantage because, in many practical applications, it is desired to recover organisms which are injured or "stressed" (e.g. when attempting to recover pathogens from food samples) due to exposure to sub-optimal conditions (of temperature, pH, or the like).

Allen et al (1978 Nature 272, 56-58) disclosed that phosphonopeptides possessed antibacterial properties. In particular, the compound L-alanyl-L-1-aminoethylphosphonic acid (called "alaphosphin") was shown to be a reasonably potent anti-bacterial agent which was believed to cause inhibition of peptidoglycan synthesis. Alaphosphin consists of the L stereoisomer of alanine, coupled to L-1-aminoethylphosphonic acid (AEP), the —COOH group of the alanine and the amino group of AEP condensing to form a peptide bond. These original findings were further developed by Atherton et al, (1979 Antimicrob. Agents and Chemother. 15, 677-683) and by Allen et al, (1979 Antimicrob. Agents and Chemother. 16, 306-313). However, alaphospin was never widely adopted as an antibiotic, and was not proposed for use as a selective agent. In particular, antibiotics are generally intended to be "broad spectrum", so as to kill a wide range of bacteria, which renders their use as selective agents in diagnostic microbiology unlikely.

SUMMARY OF THE INVENTION

In a first aspect the invention provides a method of selectively inhibiting the growth of non-target cells in a mixed population of target and non-target cells, the method comprising the steps of: (a) contacting the mixed population with a selective agent which comprises a carrier moiety linked by a scissile linkage to a toxic moiety; wherein the selective agent is able to enter non-target cells in which the scissile linkage is cleaved, releasing the toxic moiety to exert a toxic effect on the non-target cells causing inhibition of the growth of the non-target cells, whereas the selective agent is unable to enter target cells and/or the scissile linkage is not cleaved in target cells and/or the toxic moiety, if released from the selective agent, does not exert a toxic effect on the target cell; and (b) culturing the cells in conditions which allow for growth of non-inhibited cells.

The cells may be eukaryotic cells (e.g. mammalian cells, fungal cells or yeast cells) but more typically will be bacterial cells. In particular, the target and non-target cells will normally both comprise bacteria, and advantageously the target cell may be a Gram negative organism (e.g. *Salmonella* spp.) and the non-target cells will also comprise Gram negative organisms (e.g. *E. coli*).

The target cells will typically be those of a organism whose presence it is desired to detect among the mixed population. For example the target cells may be a particular pathogenic species or genus, whilst the non-target cells (which are not of interest) may be cells representative of the normal gut or skin flora of a subject, from whom a sample containing the mixed population has been obtained. Alternatively, the sample may be, for example, a sample of a foodstuff or drink for human or animal consumption. Typically the non-target cells will be present in greater numbers than the target cells, hence it will be desirable selectively to inhibit the growth of the non-target cells so as to facilitate detection of the target cells, which would otherwise tend to be outgrown and so masked by the non-target cells. This is of particular importance during pre-enrichment when it is possible that the target cell may be injured or stressed and undergoes an extended lag-phase as the cell repairs any injury suffered during the manufacture or preparation of food-stuffs. A proportion of the total population of competitors will not suffer any injury and will not enter a lag-phase when inoculated into the pre-enrichment broth. These can grow quickly and, through a mechanism known as the Jameson Effect (Jameson 1962, J. Hygiene Cambridge 60, 193-207), can prevent the target cell from growing before it has left the lag-phase and begun to multiply. This can severely limit the likelihood of detecting the target cell on subsequent sub-culture.

It will be apparent from the foregoing that there may be more than one basis for the selectivity of the selective agent, one or more of which may operate for a particular selective agent/mixed population combination. One basis of selectivity (which may be employed in isolation or, more preferably, in conjunction with another basis of selectivity) is that of selective uptake by non-target cells, such that the selective agent accumulates in non-target cells but does not accumulate at toxic concentration in target cells. Conveniently selective uptake may be achieved by making use of uptake mechanisms (especially uptake enzymes such as permeases) operable in the non-target cell but not present in the target cell. In one convenient embodiment, the selective agent enters non-target cells by means of a dipeptide, tri-peptide or oligopeptide permease. Thus, the selective agent may desirably comprise a carrier moiety which is efficiently processed by an uptake mechanism in non-target cells.

Another basis of selectivity (which may be employed in isolation or in combination with a different basis) comprises use of a selective agent having a scissile linkage which is cleavable by non-target cells but is not cleavable by target cells. Conveniently, cleavage of the scissile linkage is effected by an enzyme or combination of enzymes expressed by the non-target cells but not by the target cells.

In certain embodiments the scissile linkage desirably comprises a peptide bond, cleavable by a peptidase (preferably an aminopeptidase) expressed by non-target cells but not by target cells. Typically the peptide bond will be formed by the α-COOH group of an amino acid or amino acid analogue, but it is possible that the peptide bond may be formed by a β-COOH group (e.g. aspartic acid) or δ-COOH-group (e.g. glutamic acid).

Advantageously the selective agent comprises one or more amino acid residues (including unusual amino acids such as hydroxyproline and pyroglutamic acid) or amino acid residue analogues. A number of amino acid residue analogues suitable for inclusion in the selective agent are described by Allen et al or Atherton et al, cited above.

Table 1 identifies a number of enzymes which are present in some bacteria, but not in others, and which might therefore be suitable for cleaving a toxic moiety from a selective agent and allowing the selective agent to inhibit the growth of non-target cells over target cells. In general amino-peptidases are preferred to glycosidases, and preferred selective agents therefore comprise L-amino acid residues or analogues thereof. Particularly preferred (especially in the context of selective media for the growth of *Salmonella* spp.) are selective agents cleavable by pyrrolidonylarylamidases.

TABLE 1

| | Enzyme Classification Number | Substrate |
|---|---|---|
| Aminopeptidases | | |
| prolyl aminopeptidase | 3.4.11.5 | L-prolyl- AEP |
| leucyl aminopeptidase | 3.4.11.10 | L-leucyl- AEP |
| pyrrolidonylarylamidase | 3.4.19.3 | L-pyrrolidonyl- AEP |
| Glycosidases | | |
| α-galactosidase | 3.2.1.22 | AEP-α-galactoside |
| β-galactosidase | 3.2.1.23 | AEP-β-galactoside |
| β-glucuronidase | 3.3.1.31 | AEP-β-glucuronide |
| 6-phospho-β-galactosidase | 3.2.1.85 | AEP-β-galactosides |
| 6-phospho-β-glucosidase | 3.2.1.86 | AEP-β-glucosides, |

It will generally be preferred that when cleaved from the carrier moiety, the toxic moiety will tend to remain within the non-target cell or, after lysis of the non-target cell, remain covalently associated with lysed remnants of the non-target cell. In this way, should the only basis for selectivity between non-target and target cells be the respective ability or inability to cleave the scissile linkage between the carrier moiety and the toxic moiety, the toxic moiety (once cleaved, from the carrier moiety inside a non-target cell) will not be released into the extracellular medium and so will not exert any toxic effect on the target cells. Alternatively, if released from the non-target cell (or used remnants thereof), the toxic moiety should preferably be highly charged, which tends to prevent passive entry of the free toxic moiety across the cell membrance of target cell.

Accordingly, in preferred embodiments the toxic moiety should have a high charge density (i.e. be highly charged) at the pH and under the conditions in which the selective agent is contacted with the mixed population. This also prevents the toxic moiety from migrating through the lipid bilayer of the cell envelope of the non-target cell and into the extra-cellular environment.

For present purposes a toxic moiety may be considered as having a high charge density if it has a negative log octanol/water partition coefficient, as determined by the method of Meylan & Howard (1995 Journal of Pharmaceutical Science 84, 83-92).

By way of explanation, the partition coefficient (log P) of a solute is determined most frequently using an octanol and water Mixture. The concentration of the solute is measured in both phases and expressed as a number according the equation: log P=log $[(x)_{octanol}/(x)_{water}]$ (e.g. Leo et al 1971 Chemical Reviews 71, 526-616, Meylan and Howard 1995, cited above).

Those compounds that have a positive Log P are more soluble in lipids than in water, while those with a negative Log P are more soluble in water than in lipids.

The majority of biocides have positive Log P, and this is necessary property of membrane active compounds that enable them to disrupt the functions of the cytoplasmic membrane of the cell. By contrast, those compounds with negative Log P are not membrane active and are prevented from entering the cell due to the charge associated with the molecule that prevents them crossing the cytoplasmic membrane to their site of action in the cytoplasm.

Table 2 below shows the log octanol/water partition coefficient for various toxic moieties: those having a negative value are especially advantageous for incorporation in a selective agent for use in accordance with the present invention.

TABLE 2

| Toxic Moiety | Leg Partition Coefficient |
|---|---|
| 2-phenylethanol | 1.36[a] |
| Phenol | 0.88[a] |
| Dowicide 9 (4-chloro-2-cyclopentylphenol) | 4.48[b] |
| 4-hydroxybenzoic acid | 2.23[a] |
| 4-methylphenol | 1.93[a] |
| 4-bromophenol | 2.59[a] |
| 2,4-dichlorophenol | 2.80[b] |
| 4-chloro-2-nitrophenol | 2.55[b] |
| 2-nitophenol | 2.00[a] |
| ethyl-4-hydroxybenzoic acid | 2.45[b] |
| Thiophenol | 2.52[a] |
| Aniline | 0.94[a] |
| 2-mercaptopyridine | 1.50[b] |
| 4-[N-(mercaptoethyl)]aminipyridine-2,6-dicarboxylic acid | 0.63 |
| 8-hydroxyquinoline | 1.75[a] |
| 8-hydroxyquinoline-5-sulphonic acid | −1.50[b] |
| L-1-aminoethylphosphonic acid | −1.75[b] |
| Sulfacetamide | −0.60[b] |
| Sulfanilamide | −0.78[a] |
| Sulfanillic acid | −2.08[b] |
| $N^3$-4-methoxyfumaroyl-L-2,3-diaminopropionic acid | −2.90[b] |

[a]Leo et al (1971);
[b]calculated by the method in Meylan & Howard (1995).

Preferred toxic moieties include 1-aminoalkyl compounds (especially acids and salts) especially amino lower alkyl compounds (i.e. those comprising a $C_{1-4}$ alkyl group, preferably an ethyl group), especially acids and salts. Preferred toxic moieties include aminoalkyl phosphonic acids/salts such as 1-aminoethyl phosphonic acid (AEP) and aminoalkyl sulphonic acids/salts, such as 1-aminoethyl sulphonic acid (AES). These aminoalkyl compounds possess a degree of structural similarity with amino acids, and may therefore be considered, for present purposes, as amino acid analogues, and when incorporated into a selective agent (preferably by a peptide bond) may be considered as amino acid residue analogues. Indeed, highly charged amino acid analogues may generally be useful as toxic moieties in the method of the invention. Other examples which may be useful are glutamine analogues, especially glutamine analogues which inhibit the enzyme glucosamine-6-phosphate synthase. Suitable analogues include, for example, $N^3$-(4-methoxyfumargyl)-L-2,3-diaminopropanoic acid (abbreviated as FMDP) and related compounds disclosed in GB 2282602.

Conveniently the 1-amino group of the preferred aminoalkyl acids/salts may be joined to a carboxyl group of a carrier moiety to form a peptide bond scissile linkage, cleavable by a peptidase (advantageously an aminopeptidase).

As an alternative the selective agent may comprise an a glycoside, especially an N-glycoside, in which the carrier moiety is an N-sugar. For example, suitable selective agents may comprise a 1-aminoalkyl compound as aforementioned, such as AEP or AES or salts thereof, covalently coupled to the N-sugar via the α-amino group.

In certain embodiments the selective agent resembles a di-, tri- or oligopeptide. In one preferred embodiment, the selective agent resembles a dipeptide, with the carrier moiety comprising an amino acid residue, and the toxic moiety comprising an amino acid residue analogue. Desirably the one or amino acid residues in the carrier moiety are the L stereoisomer. Equally, a preferred amino acid residue analogue of the toxic moiety is an L stereoisomer.

In a preferred embodiment, the carrier moiety comprises an L-alanine residue which, desirably, is joined via a peptide bond via its COOH group to an L-alanine residue analogue (such as AEP or AES). Thus in one preferred embodiment the selective agent comprises a dipeptide consisting of an L-alanine residue linked to an L-alanine residue analogue, the selective agent being an alanyl-alanine analogue. In such an embodiment, the enzyme L-alanyl aminopeptidase ("LALA") can cleave the peptide bond (i.e. the scissile linkage) between the L-alanine residue and the L-alanine residue analogue, releasing the L-alanine analogue to exert a toxic effect.

Such embodiments are particularly convenient, as the enzyme LALA is not expressed by all bacteria, and thus can be used as a basis for selectivity. In addition, L-alanine analogues are effective growth inhibitors, acting as essentially irreversible inhibitors of the enzymes involved in peptidoglycan synthesis. The L-alanine analogues become tightly associated with the enzymes, and so tend not to be released into the extracellular environment in a free, toxic form, even after lysis of the non-target cell.

The term 'analogue' as used herein, will therefore be understood by those skilled in the art to refer to a molecule which shares a reasonable degree of structural similarity with the parent molecule of which it is an analogue and, in particular, an enzyme which acts on the parent molecule will generally bind to an analogue thereof. However, due to the differences between the parent molecule and the analogue, the enzyme may not process the two entities in the same way. For example, whilst the parent molecule will be a substrate for the enzyme and will be released from the enzyme once the enzyme-catalysed reaction has taken place, the analogue will not necessarily be subject to the enzyme-catalysed reaction undergone by the parent molecule, and so may remain bound to the enzyme and act as a potent inhibitor thereof.

However, those skilled in the art will appreciate that a large number of other peptidases (especially aminopeptidases) are expressed by particular groups of organisms and selective agents for use in the invention may comprise other amino acid residues or amino acid residue analogues. Examples of amino acids or analogues suitable for inclusion as the carrier moiety include valine, proline and pyroglutamic acid (pyr). Thus, for example, proline-AEP, proline-AES or Pyr-AEP and Pyr-AES represent other suitable selective agents for use in the invention.

A number of bacteria possess a dipeptide, tripeptide or oligopeptide permease, which facilitates entry into the cell of dipeptide, tripeptide or oligopeptide selective agents, which allows relatively low concentrations of selective agent to be used effectively.

The method of the invention may be applied in any manner of situations where it is desired to cause inhibition of part of a mixed population of cells. Examples include: selective inhibition of coliforms (especially *E. coli*) in mixed populations of bacteria in clinical samples, so as to facilitate isolation of *Campylobacter* (which do not possess L-alanyl aminopeptidase activity and which will, if present, typically constitute only a very minor portion of the mixed population); selective inhibition of Gram negative bacteria (especially coliforms) to facilitate isolation of pathogenic Gram positive organisms (such as *Staph. aureus* which is L-alanyl aminopeptidase-ve): and distinguishing in clinical samples between the presence of *Haemophilus influenzae* and *Haemophilus parainfluenzae*, (which distinction has implications for prognosis and treatment), by culturing samples in suitable conditions with a selective agent so as to cause selective inhibition of one of the aforesaid organisms (*H. influenzae* has no relevant aminopeptidase activity, whilst *H. parainfluenzae* does possess a relevant aminopeptidase which will cleave compounds such as alaphosphin).

A further particular application of the present invention, which is especially preferred, is to selectivity inhibit *Citrobacter* and other coliforms in mixed populations of bacteria so as to facilitate detection, and optionally isolation, of *Salmonella* spp: e.g. from food samples, so as to assist in diagnosis of disease and to identify contaminated food samples in public health measures. In such an embodiment, it may be desirable to use a selective agent comprising a toxic moiety linked via a peptide bond to pyroglutamic acid, since the inventors have noted that *Salmonella* spp generally lacked a pyroglutamyl peptidase, whilst such an enzyme is present in most coliforms, so that the non-target organisms will cleave the toxic moiety from the selective agent.

Conventionally, when testing samples of food and the like for possible contamination with *Salmonella*, it is usual to carry out a two-step incubation. In the first step about 25 grams of sample is usual diluted 1/10 in 225 mls of pre-enrichment broth and incubated for about 16 hours or overnight. The pre-enrichment broth usually does not contain any selective agent. This is because *Salmonella* organisms possibly present in the sample will frequently be "stressed" (that is are weakened having been exposed to suboptimal conditions of temperature, pH and the like). In such a "stressed" condition the presence of a selective agent at a normally sub-lethal concentration may often actually cause cell death.

Incubation in the pre-enrichment medium allows any stressed cells to recover. The cultures are then further diluted (e.g. 100 µl into 10 mls) into an enrichment medium which contains a selective agent at a concentration which allows *Salmonella* spp. to grow, whilst inhibiting (i.e. preventing any net increase in viable cell numbers) competitor coliform organisms. In practice, most conventional selective agents also inhibit the growth of *Salmonella* spp, but to a significantly lesser extent than they inhibit competitor organisms.

An advantage of the present invention, in preferred embodiments, is that a selective agent can be used which is substantially non-inhibitory to *Salmonella* spp, even in a stressed state. Accordingly it is possible to include the selective agent in the initial medium and/or to reduce the overall culture time required for *Salmonella* spp organisms (if present in the original sample) to attain the cell density required to give a positive result in any asay for their presence (e.g. ELISA, PCR etc), since their growth is not inhibited. This permits the results to be made available sooner (following receipt of the sample) than has hitherto been the case.

In preferred embodiments of the invention the selective agent causes inhibition of the non-target cells but is essentially non-inhibitory to target cells, whether they are in stressed or unstressed condition.

When bacterial cells are placed in a suitable growth medium there is a 'lag phase' during which the net number of viable bacterial cells does not increase, or increases only slowly. After the lag phase, the culture enters an exponential growth phase in which the mean "generation time" (that is, the mean time taken for a number of cells to proceed from formation to fission) is at its shortest.

As an illustration of what is considered "essentially non-inhibitory", a selective agent will normally be considered essentially non-inhibitory to target cells at a particular concentration if it causes an increase in the lag phase of less than 25%, preferably less than 20% and more preferably less than 15% and if it causes an increase in the mean generation time, during the exponential growth phase, of less than 20%, preferably less than 10%, and more preferably less than 5%.

Those skilled in the art will appreciate that performance of the method of the first aspect of the invention may allow conclusions to be made regarding the identity of organisms which are able to grow successfully in the selective growth conditions. Thus, in some embodiments, the invention may comprise the further step of identifying target cell organisms which are able to grow in a culture comprising the selective agent. Alternatively, or additionally, the method may comprise the step of isolating colonies of the target cell organisms which are able to grow in a culture comprising the selective agent. Such methods of identification and/or isolation are routine for those skilled in the art and form no part of the present invention.

In a second aspect the invention provides a selective medium for selective inhibition of non-target cells in a mixed population of non-target cells and target cells, the medium comprising a selective agent, which selective agent comprises a carrier moiety linked via a scissile linkage to a toxic moiety. Preferably the selective agent is as defined above. The selective medium may be liquid or solid, and may comprise any of the components which may conventionally be included in media, such as peptones, yeast extract, agar (or other solidifying agent), salts, buffers, indicator dyes and the like.

In a third aspect, the invention provides a kit for causing selective inhibition of non-target cells in a mixed population comprising non-target cells and target cells, the kit comprising a selective agent as defined above and instructions for use in accordance with the method of the first aspect of the invention.

In preferred embodiments, the kit will comprise a medium in accordance with the second aspect of the invention defined above or, as an alternative, ingredients for preparing a selective medium in accordance with the invention.

The various aspects of the invention will now be further described by way of illustrative example and with reference to the accompanying drawings in which.

Figure 1A:
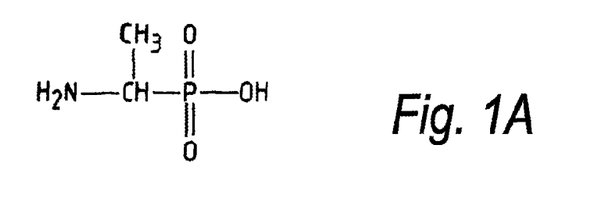
FIG. 1*a* is a representation of the chemical structure a preferred toxic moiety (AEP) for use in the method of the invention.
Figure 1B:
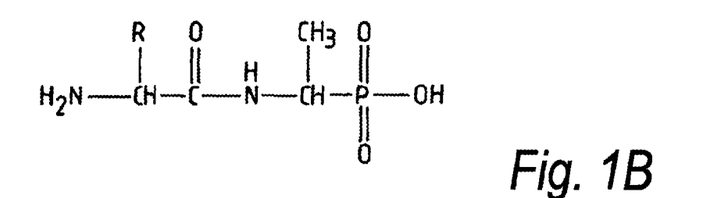
FIG. 1*b* is a representation of the chemical structure of a preferred selective agent, comprising the toxic moiety illustrated in FIG. 1*a;*
Figure 1C:
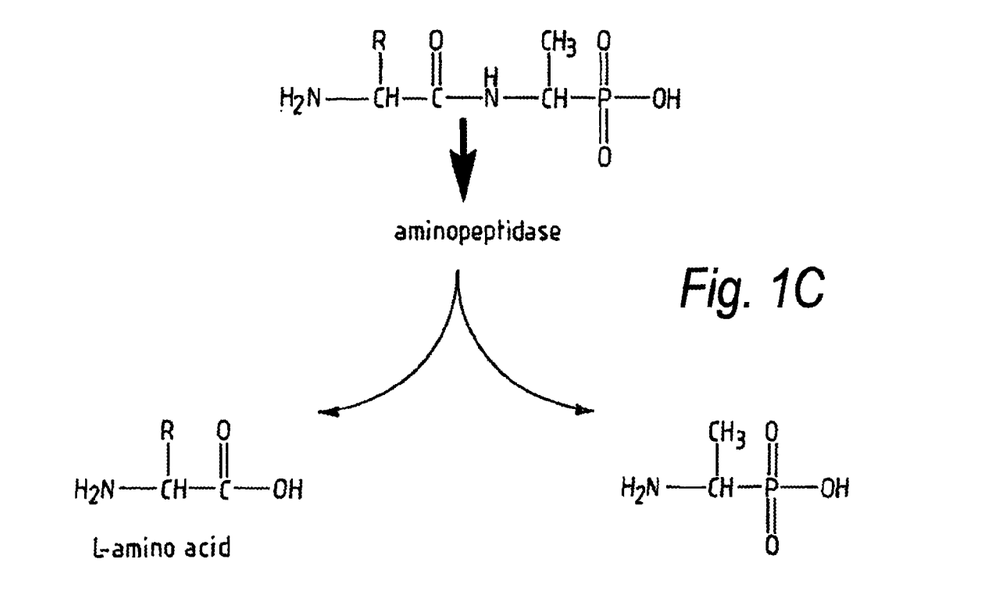
FIG. 1*e* illustrates cleavage of the selective agent shown in FIG. 1*b*, by an aminopeptidase, to release the toxic moiety shown in FIG. 1*a;*

In FIGS. 1*b* and 1*c*, R may be inter alia, any of the side chains of the amino acid residues. In FIG. 1*b*, where R is $CH_3$, the selective agent is alaphosphin, and the released L-amino acid in FIG. 1*c* is L-alanine.

EXAMPLES

In the Examples that follow, a large number of bacterial strains are mentioned. The letters "OCC" are an abbreviation for 'Oxoid Culture Collection', and these organisms were obtained from within the Applicant's own laboratories. However, in most instances, identical (or at least closely equivalent) organisms are obtainable from publicly available collections such as the National Collection of Type Cultures (NCTC, Central Public Health Laboratory, Colindale, London) or the American Type Culture Collection (ATCC, Manassas, Va., USA) or elsewhere, as shown in Table 3 below. In any event, these organisms are merely representative samples and other strains, typical of the species in question, could equally be used for the purposes of illustrating the invention.

TABLE 3

| Strain | Oxoid Culture Collection Number (OCC) | NCTC | ATCC | Other |
|---|---|---|---|---|
| *Citrobacter freundii* | | | | PHLS Poole 93703 |
| *Citrobacter freundii* | 261 | | | |
| *Enterobacter aerogenes* | 720 | 10006 | 13048 | |
| *Enterobacter cloacae* | 760 | 10005 | 13047 | |
| *Escherichia coli* | 122 | | | |
| *Escherichia coli* O 157:H7 VT-ve | 1872 | 12900 | | |
| *Escherichia coli* | | 10090 | | |
| *Escherichia coli* | 402 | 9001 | 11775 | |
| *Escherichia coli* | 2129 | | | |
| *Bacillus subtilis* | 214 | | 6633 | |
| *Enterococcus faecalis* | 640 | | 29212 | |
| *Klebsiella pneumoniae* | | | | CMCC 3077 |
| *Klebsiella pneumoniae* | 411 | | 29665 | |
| *Staphylococcus aureus* | 102 | | | |
| *Salmonella enteritidis* | 723 | | 25928 | |
| *Salmonella indiana* | 2412 | 11304 | | |
| *Salmonella typhimurium* | 722 | 12023 | 14028 | |
| *Salmonella virchow* | 703 | 5742 | | |

TABLE 3-continued

| Strain | Oxoid Culture Collection Number (OCC) | NCTC | ATCC | Other |
|---|---|---|---|---|
| Salmonella typhimurium | 1792 | | | CMCC 3073 |
| Salmonella worthington | 634 | | | |

Example 1

A number of experiments were conducted to demonstrate inhibition of growth of certain bacteria and selective inhibition of bacteria in mixed populations of cells. In these experiments, described in Examples 1-5, bacteria were incubated on nutrient agar (CM3) supplemented with alaphosphin or AEP (both obtained from Fluka). The experiments were conducted as follows: nutrient agar medium was autoclaved and, on cooling (but prior to setting) filter-sterilised alaphosphin or AEP were incorporated at final concentrations of 1 mM, 2 mM, 5 mM and 10 mM, and the medium used to pour plates. Control plates were prepared using nutrient agar without alaphosphin or AEP. A single colony of the organism under test was inoculated in 10 ml of nutrient broth and incubated (without agitation) at 37° C. for 4 hours. The culture was then diluted 1:1000 (in nutrient broth) and the resulting dilution used to inoculate the prepared plates using a variant of the "econometric" method (Mossel et al, 1983 J. Appl. Bacteriol. 54, 313-327) with 4 streaks from a 1 µl inoculating loop. (Where mixed populations where prepared, as in Examples 6-8, 1 µl samples were taken from the respective 1:1000 dilutions of the separate cultures, the 1 µl samples mixed together and then used to inoculate the plates a described previously).

Figure 2:
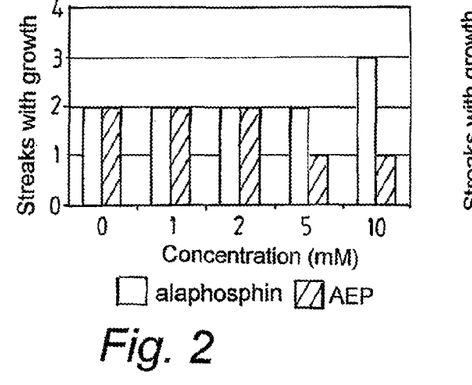
FIGS. 2-12 are bar charts showing the amount of growth of various organisms, in pure or mixed culture, in the presence of AEP or alaphosphin.

In example 1 the sensitivity of *Bacillus subtlis* strain OCC 214 to alaphosphin or AEP was investigated. The results are shown in FIG. 2, which is a bar chart showing the number of streaks demonstrating bacterial growth at 0-10 mM concentrations of alaphosphin (blank columns) or AEP (shaded columns). The results indicate that *B. sublilis* OCC214 is inhibited by AEP at a concentration of 5 mM or more, but is completely insensitive to alaphosphin and/or cannot hydrolyse alaphosphin to release AEP. The organism is known to be LALA-ve, so the observations agree with the known characteristics of the organism.

Example 2

Figure 3:
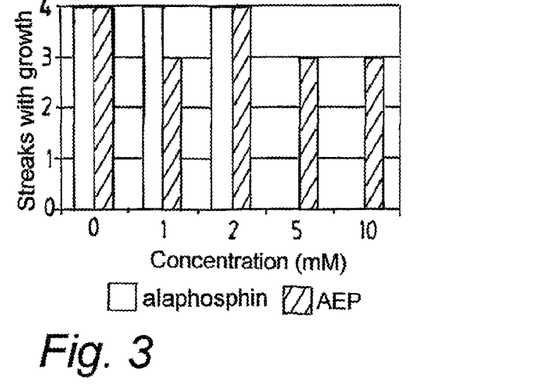

Example 1 was repeated, using *Salmonella typhimurium* OCC 1870 as the test organism. The results are shown in FIG. 3, which uses the same key as FIG. 2. *S. typhimurium* OCC 1870 was found to be resistant to AEP at concentrations as high as 10 mM. However, the organism is known to be LALA+, and alaphosphin was found to be completely inhibitory at concentrations of 5 mM or more, indicating that alaphosphin is taken up by the cell and hydrolysed, but that AEP itself cannot enter the cell.

Example 3

Figure 4:
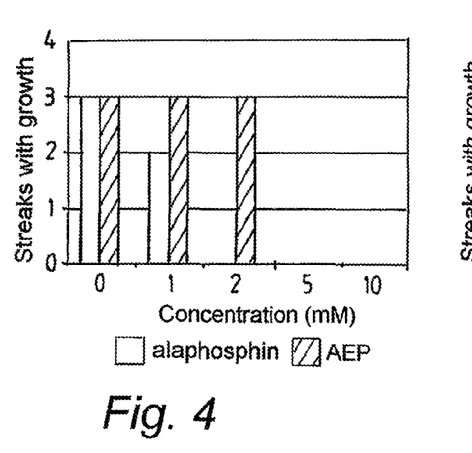

Example 1 was repeated using *Enterococcus faecalis* OCC 640 as the test organism. The results are shown in FIG. 4. The organism was found to be completely inhibited by AEP at a concentration of 5 mM or more, indicating that the organism expresses an uptake polypeptide (possibly an L-alanine permease) which accepts and transports AEP. The organism is LALA+ and is completely inhibited by alaphosphin at a concentration of 2 mM or more.

Example 4

Figure 5:
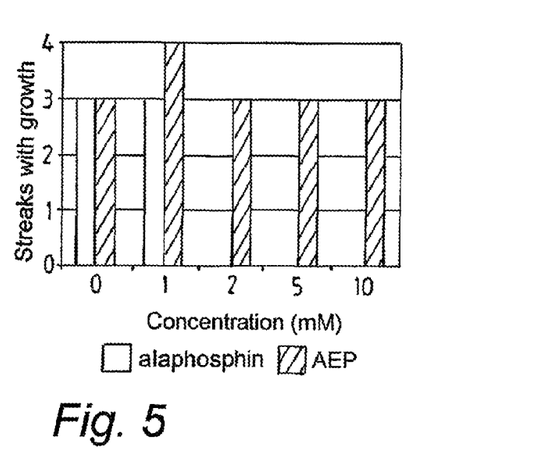

Example 1 was repeated using *Klebsiella pneumoniae* CMCC 3077 as the test organism. The results are shown in FIG. 5, and are qualitatively similar to those obtained in example 2. *K. pneumoniae* CMCC 3077 is LALA+ve and is completely inhibited by alaphosphin at 2 mM or more, but is insensitive to AEP at concentrations up to 10 mM.

Example 5

Figure 6:
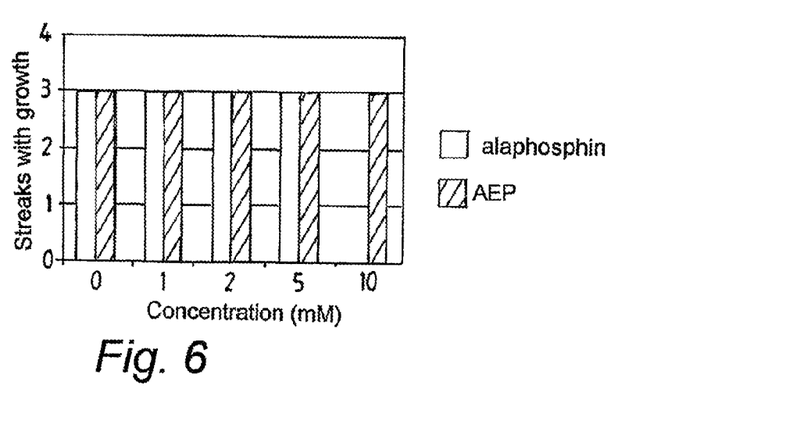

Example 1 was repeated using *Staphylococcus aureus* OCC 102 as the test organism. The results are shown in FIG. 6. *S. aureus* OCC 102 was completely insensitive to AEP at all concentrations tested, but was completely inhibited by alaphosphin at 10 mM. This indicates that the organism can take up alaphosphin and hydrolyse it, but less efficiently than the organisms tested in Examples 2-4.

Example 6

Figure 7:
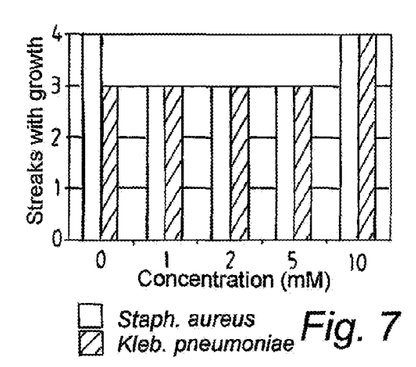
Figure 8:
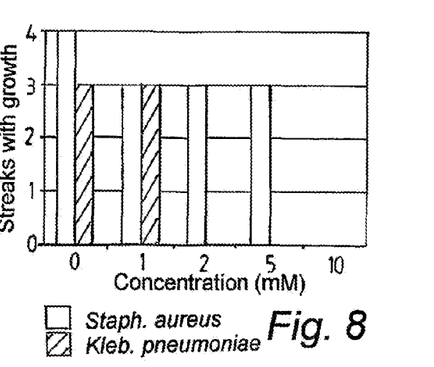

Example 1 was repeated, this time using a mixed culture of *K. pneumoniae* CMCC 3077 and *S. aureus* OCC 102. The results for growth in the presence of AEP or alaphosphin are shown in FIGS. 7 and 8 respectively: empty columns represent growth of *S. aureus*, the shaded columns represent growth of *K. pneumoniae*. As predicted from Examples 4 and 5, neither organism was inhibited by AEP in mixed culture. In the presence of alaphosphin, *K. pneumoniae* growth was completely inhibited above 1 mM, whilst *S. aureus* was inhibited only by 10 mM alaphosphin. Accordingly, there is a considerable alaphosphin concentration range over which *S. aureus* will readily grow whilst *K. pneumoniae* will be inhibited. Even if *K. pneumoniae* cells lyse due to the toxic effect of AEP released intracellularly, the AEP is not toxic for *S. aureus* at the concentrations involved.

Example 7

Figure 9:
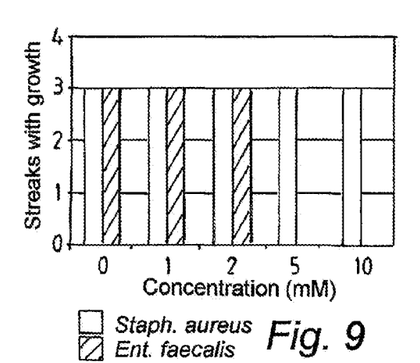
Figure 10:
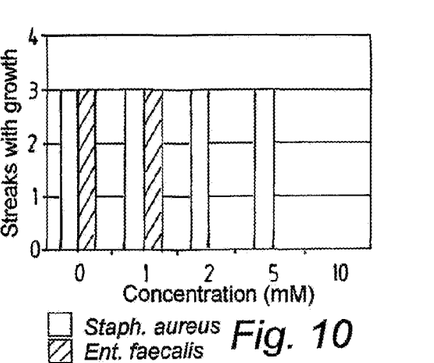

Example 6 was repeated, this time using a mixed culture of *S. aureus* OCC 102 and *E. faecalis* OCC 604, in the presence of AEP or alaphosphin. The results are shown in FIGS. 9 and 10 respectively. The empty columns represent growth of *S. aureus*, the shaded columns represent growth of *E. faecalis*. Alaphosphin at a concentration of 2 mM or more caused complete inhibition of *E. faecalis*, whilst *S. aureus* was inhibited only at a concentration of 10 mM or more. Thus alaphosphin could be used, when incorporated at an appropriate concentration in a medium, to inhibit growth of organisms such as Enterococci in samples whilst allowing Staphylococci to grow and be detected.

Example 8

Figure 11:
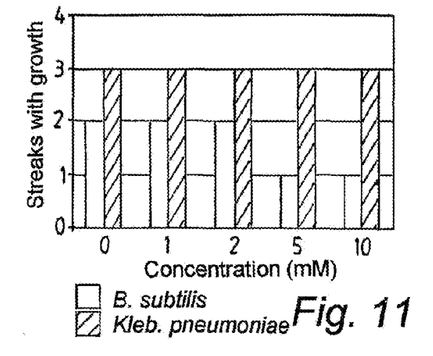
Figure 12:
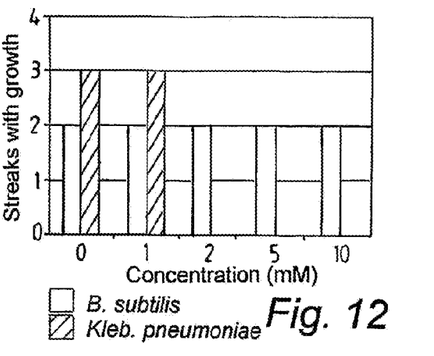

Example 6 was repeated, this time using a mixed culture of *B. subtilis* OCC 214 and *K. pneumoniae* CMCC 3077, in the presence of AEP or alaphosphin. The results are shown in FIGS. 11 and 12 respectively. The empty columns show the growth of *B. subtilis*, the shaded columns denote growth of *K. pneumoniae*. FIG. 11 shows that *K. pneumoniae* is insensitive to AEP at all the concentrations tested, whilst *B. subtilis* exhibited some sensitivity above 5 mM. FIG. 12 shows that *K. pneumoniae* was completely inhibited by alaphosphin at a concentration of 2 mM or more, whilst *B. subtilis* was insensitive to alaphosphin at this concentration range. The results indicate that hydrolysis of alaphosphin by *K. pneumoniae* does not yield sufficient free AEP to cause any inhibition of *B. subtilis*.

The above examples all relate to experiments conducted using nutrient agar, which contained peptone at 8 gms/litre. Peptone contains oligopeptides which may affect expression of oligopeptide permease and/or peptide genes. Accordingly, where the selective agent is a di-, tri- or oligopeptide, and/or the scissile linkage comprises a peptide, the type and/or concentration of peptone in the selective medium may affect the concentration of selective agent required in the medium to obtain the optimum degree of selectivity.

Example 9

Other compounds which should prove useful as a selective agent in a method in accordance with the invention are those in which the carrier moiety comprises pyroglutamic acid (Pyr), especially L-pyr. Conveniently the toxic moiety will comprise AEP. Such a selective agent should be able selectively to inhibit the growth of organisms expressing a "Pyrase" (i.e. $Pyr^+$ organisms), whilst allowing $Pyr^{-ve}$ organisms to grow. Many coliforms are $Pyr^+$ (e.g. *Citrobacter* spp., *Klebsiella* spp., *Serratia* spp. and most *Enterobacter* spp.). Thus, for example, L-pyr-AEP might be a useful selective agent in liquid media to facilitate the selective pre-enrichment step during isolation of *Salmonella* spp. from clinical or environmental samples, and subsequently in solid media for the selective isolation step.

In another embodiment L-pyr-AEP might be used for selective enrichment for $Pyr^{-ve}$ *Listeria* spp, whilst inhibiting $Pyr^+$ coliforms, enterococci and many *Bacillus* spp.

A number of experiments were performed in order to illustrate these embodiments of the invention.

Example 9A

Data and explanatory text for inclusion in Example 9 (Pyr-AEP).

This example demonstrates the inhibition, by L-pyroglutamyl-L-aminoethyl phosphonate (Pyr-AEP), of organisms genotypically similar to *Salmonella* but not *Salmonella* itself. Thus, Pyr-AEP was dissolved in deionised water (14.1 mg/ml), filter sterilised, and an amount of the solution added to autoclaved Lab-Lemco broth (20 g/l; pH 6.0) to give a final concentration of 141 µg/ml. Volumes (300 µl) of this solution were then pipetted into the wells of Bioscreen microtitre plates and 30 µl quantities of 1 in 10,000 dilutions of overnight cultures of *Citrobacter freundii, Enterobacter aerogenes, Enterobacter cloacae, Salmonella typhimurium* and *Salmonella worthington* added (note that this further dilution reduced the concentration of Pyr-AEP to 128 g/ml). Plates were then covered, incubated at 37° C., and the opacity of the organism suspensions measured using a Bioscreen instrument (a semi automated microbiological growth analyser, available from Thermolabsystems, Ashford, Middlesex, UK.). Growth of the *Salmonella* strains, which do not contain L-pyroglutamyl hydrolase (also referred to as a pyrrolidonylarylamidase, E.C. 3.4.19.3), was not inhibited by Pyr-AEP whereas the other strains tested, which do contain the enzyme, were inhibited.

Figure 13:
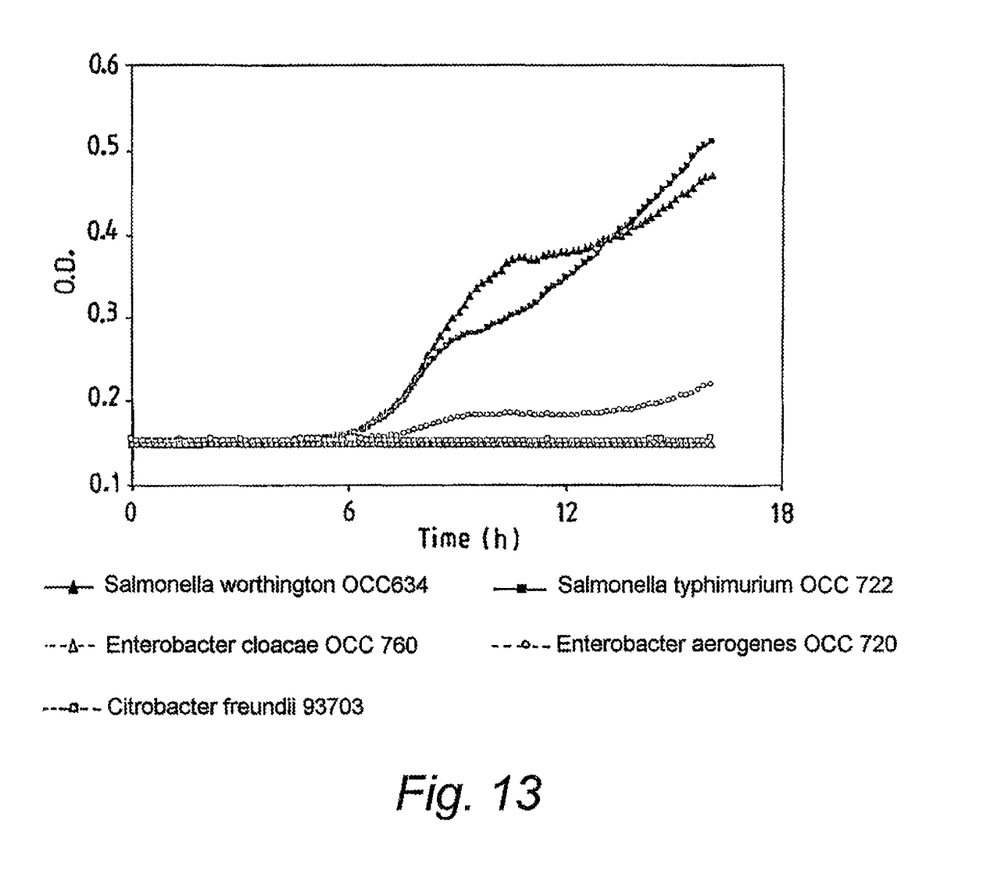
FIGS. 13, and 16-19 are graphs showing growth of various bacteria (as measured by Optical Density) against time (hours) under various conditions.

The results are shown in FIG. 13, which is a graph of optical density against time (in hours). The optical density readings were taken in "wide band" (wb) mode, i.e. using white light without any filter.

Example 9B

In addition to the pure culture work described above, mixed culture experiments were performed.

L-Pyroglutamyl-L-aminoethylphosphonate was added to Nutrient Broth No. 2 (final concentration=128 µg/ml) contained in a universal tube in a water bath at 37° C. *Citrobacter freundii* OCC 370 and *Salmonella typhimurium* OCC 626 were grown overnight in Nutrient Broth No. 2 at 37° C., diluted 1 in 1000 in Maximal Recovery Diluent and amounts added to the Nutrient Broth to give final concentrations of about $10^4$ cfu/ml of each organism. At intervals samples were taken and spread on XLD and the number of red colonies with black centres enumerated as *Salmonella* and yellow ones as *Citrobacter*.

Figure 14:
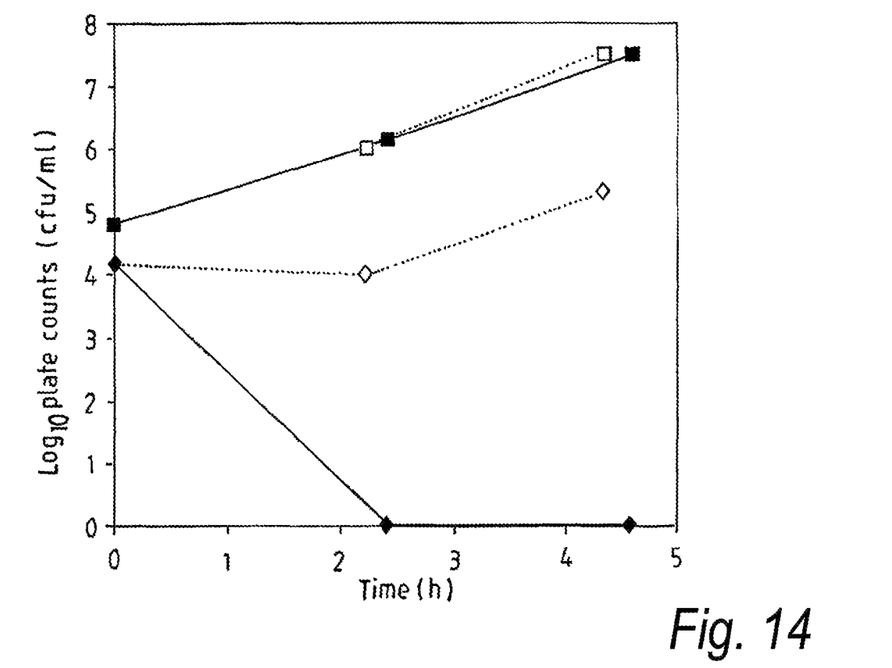
FIGS. 14 and 15 are graphs showing growth of various bacteria (as measured by $Log_{10}$ Cfu/ml) against time (hours) under various conditions.

The results are shown in FIG. 14, which is a graph of $Log_{10}$ viable count (cfu/ml) against time (in hours). The plots for *C. freundii* are shown by lozenge symbols, whilst those for *S. typhimurium* are shown by squares. Filled symbols and solid lines show results in the presence of Pyr-AEP, empty symbols and dotted lines show results in the absence of Pyr-AEP.

The graph clearly shows that Pyr-AEP has no significant effect on the growth of *Salmonella*, but is completely inhibitory for *Citrobacter*.

Example 10

Growth curve data on the activity of alaphosphin towards *Klebsiella* spp. was generated. Particular attention was paid to measuring the kinetics of inhibition in broth culture. The media used in this work were Buffered Peptone Water, Nutrient Broth and Tryptone Soya Agar. The media were prepared according to the manufacturer's instructions.

The selective agents, AEP (Cat. No. 06655) and alaphosphin (Cat. No. 05260), were supplied by Fluka. They were dissolved in water at 0.5M concentration, filter-sterilised, and 100 µl added to 10 ml of Nutrient Broth to give a final concentration in the test medium of 5 mM of AEP or alaphosphin respectively.

*Klebsiella pneumoniae* CMCC3077 was chosen, as it is a food isolate and work had been carried out previously on this organism using alaphosphin and AEP (see preceding examples). The organism was inoculated into Nutrient Broth and incubated overnight at 37° C. The culture was diluted and inoculated into the test media so that it had a final concentration of between $1\times10^5$ cfu/ml and $1\times10^6$ cfu/ml. The test media were incubated at 37° C., and sampled at hourly intervals. The cultures were serially diluted in Buffered Peptone Water and inoculated onto Tryptone Soya Agar. These plates were incubated overnight at 37° C. and the total viable count made the next day.

Five mM AEP in Nutrient Broth had little effect on the growth of *Klebsiella pneumoniae* CMCC3077 when compared with the Nutrient Broth control. In contrast, alaphosphin was an effective selective agent for the inhibition of *Klebsiella pneumoniae* CMCC3077 and caused a two to three log reduction in the viable count in Nutrient Broth within a 4 hour period.

Figure 15:
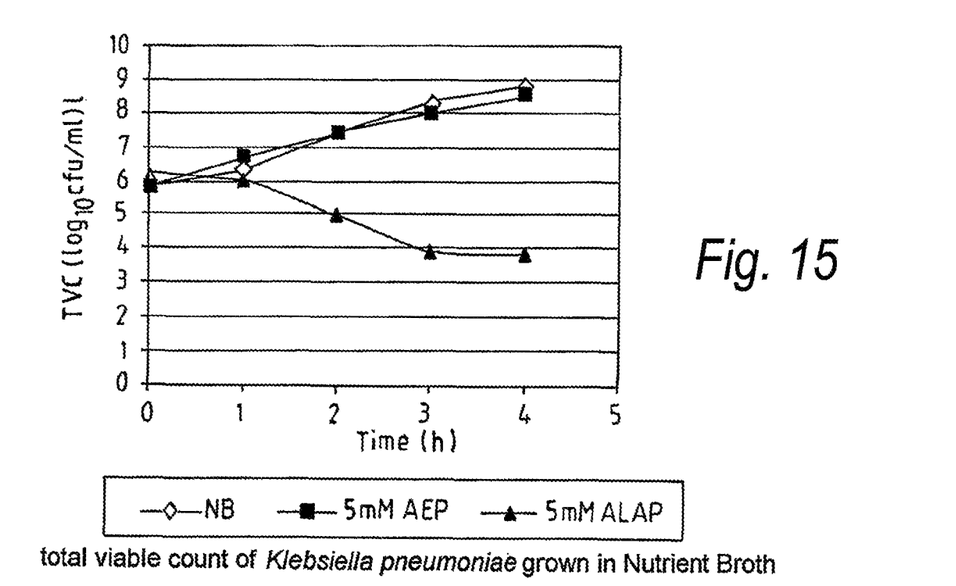

Typical results are shown in FIG. 15 which is a graph of total viable count ($log_{10}$ cfu/ml) against time (hours). The empty lozenge symbol shows the results in Nutrient Broth control media, the filled squares show the results of test media containing 5 mM AEP, and the filled triangles show the results for test media containing 5 mM alaphosphin.

The concentration of alaphosphin used in this medium was not optimised. The example illustrates that AEP peptides can significantly effect some of the organisms that compete with Salmonella spp. for nutrients in culture media, and that if the substrate is hydrolysed and AEP released in to the medium, it has minimal influence on growth rate.

Example 11

Experiments were performed to demonstrate the inhibition, by alaphosphin (Ala-AEP), of strains of *Escherichia coli* but not *Salmonella*. Thus, Ala-AEP was dissolved in deionised water (7.0 mg/ml), filter sterilised, and an amount of the solution added to autoclaved Lab-Lemco broth (20 g/l; pH 5.7) to give a concentration of 70 µg/ml. Volumes (300 µl) of this solution were then pipetted into the wells of Bioscreen microtitre plates and 30 µl quantities of 1 in 10,000 dilutions of overnight cultures added (reducing the final alaphosphin concentration to 64 µg/ml). Plates were then covered, incubated at 37° C., and the opacity of the organism suspensions measured using a Bioscreen instrument. Growth of the *Salmonella* strains was unaffected whereas the *E. coli* strains were all inhibited. In this instance, *Salmonella* are thought to be able to take up and hydrolyse the inhibigen but at much reduced rates in comparison with *E. coli*, such that the growth of the Salmonellae was not significantly inhibited.

Figure 16:
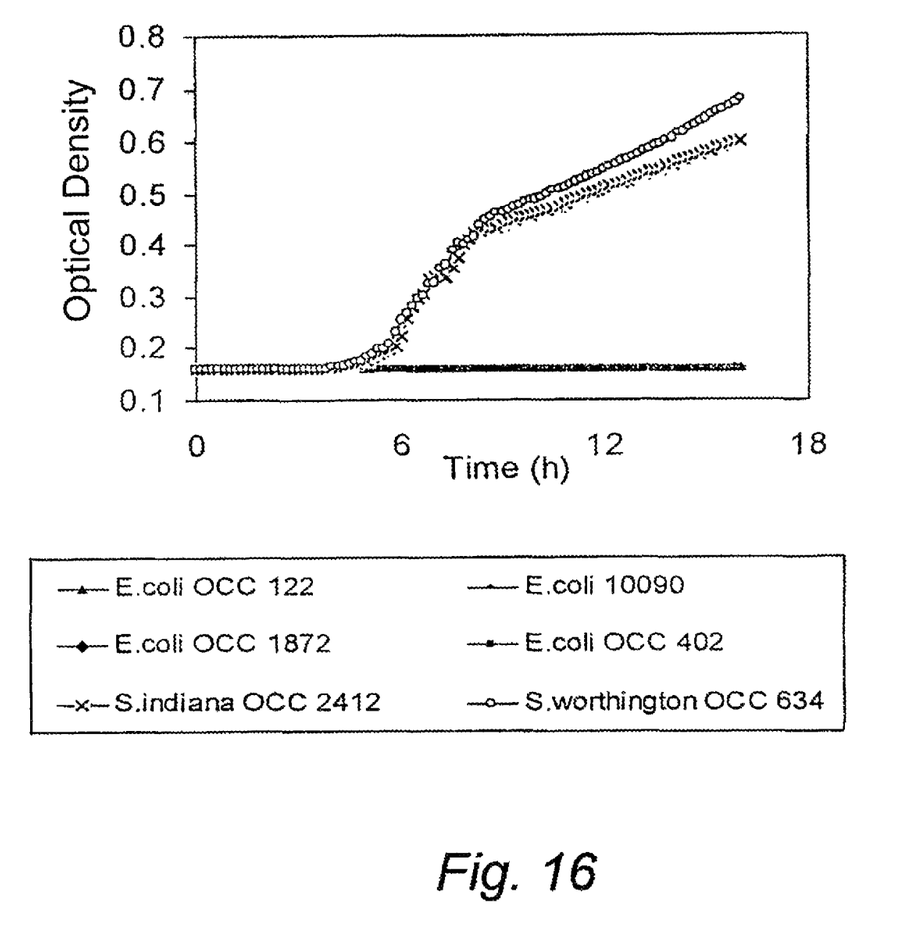

Typical results are shown in FIG. 16, which is a graph of Optical Density against time (hours). Growth of *S. indiana* OCC 2412 and *S. worthington* OCC 634 is denoted by crosses and circles respectively. Four strains of *E. coli* tested did not grow at all in the experimental conditions and the plots for these organisms therefore appear as a solid flat line.

Example 12

Conventional selective agents effectively promote the growth of target microorganisms, e.g. *Salmonella* by inhibiting the growth of non-target bacteria through the use of antibiotics, chemicals, and dyes, increased incubation temperature and reduced pH. Because of the broad and relatively non-specific nature of these treatments the growth of the target microorganism is often negatively affected. That is, the selective agent is not truly specific and causes significant inhibition of the growth of target organisms. This, in conventional methods, incubation times of 16-24 hours may be required in order to attain the required concentration of target cells for detection.

In contrast, the present invention allows for the possibility of maintaining the optimum growth rate of the target organism, which is highly advantageous in the development of rapid diagnostic tests.

The following is an example to illustrate the beneficial lower toxic properties of the new selective agents towards the target microorganism, in this case *Salmonella*. Two selective agents, cefsulodin and novobiocin, as used conventionally in *Salmonella* isolation from foods (Humphrey and Whitehead, 1992 British Poultry Science 33, 761-768) were compared with alaphosphin. All were dissolved in deionised water, filter sterilised, and an amount of the solution added to either autoclaved Lab-Lemco broth+phosphate buffer (20 g/l; pH 6.0; ala-AEP) or Buffered Peptone Water (pH 6.8; cefsulodin and novobiocin) to give final concentrations of 66, 16.5 and 11 µg/ml respectively. [The different pH values reflect the different pH optima of the selective agents (ala-AEP was also subsequently used in BPW at pH 6.8 and similar resultes obtained)]. Volumes (300 µl) were then pipetted into the wells of Bioscreen microtitre plates and 30 µl quantities of 1 in 10,000 dilutions of overnight cultures of *E. coli* OCC 2129 and *Salmonella typhimurium* OCC 722, added. Plates were then covered, incubated at 37° C., and the opacity of the organism suspensions measured using a Bioscreen instrument.

Figure 17:
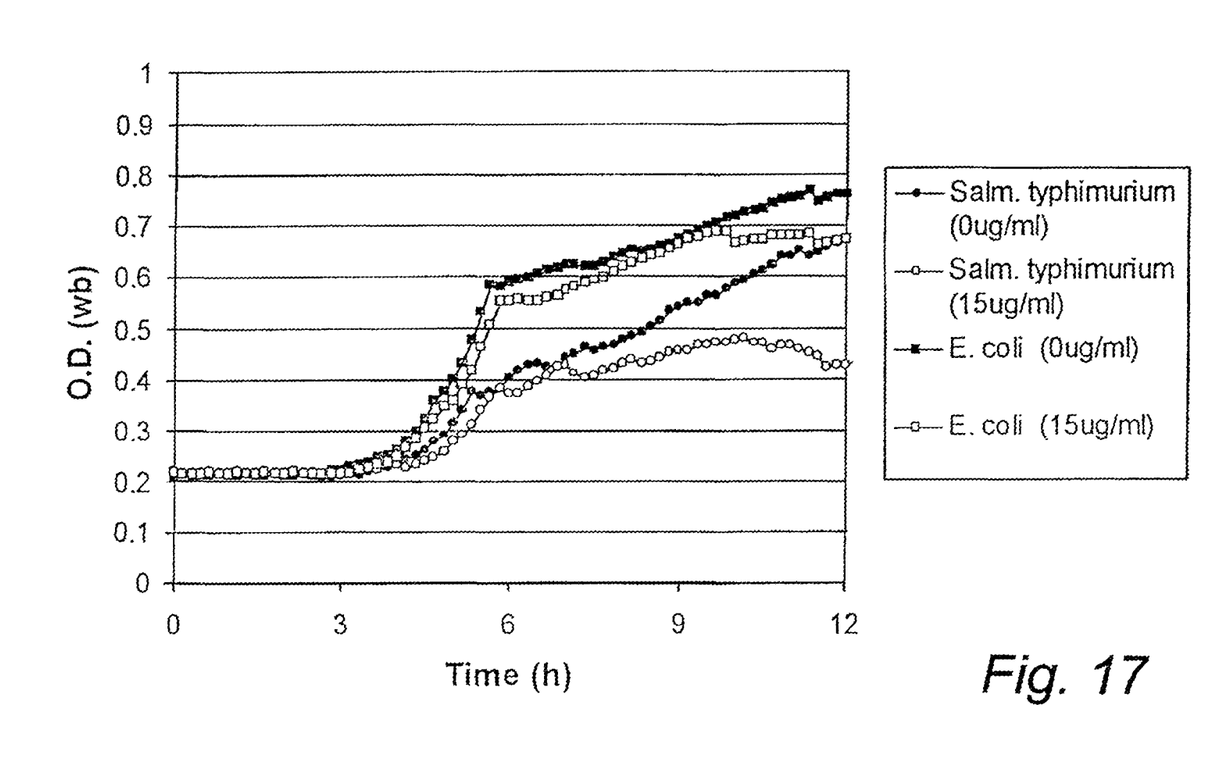
Figure 18:
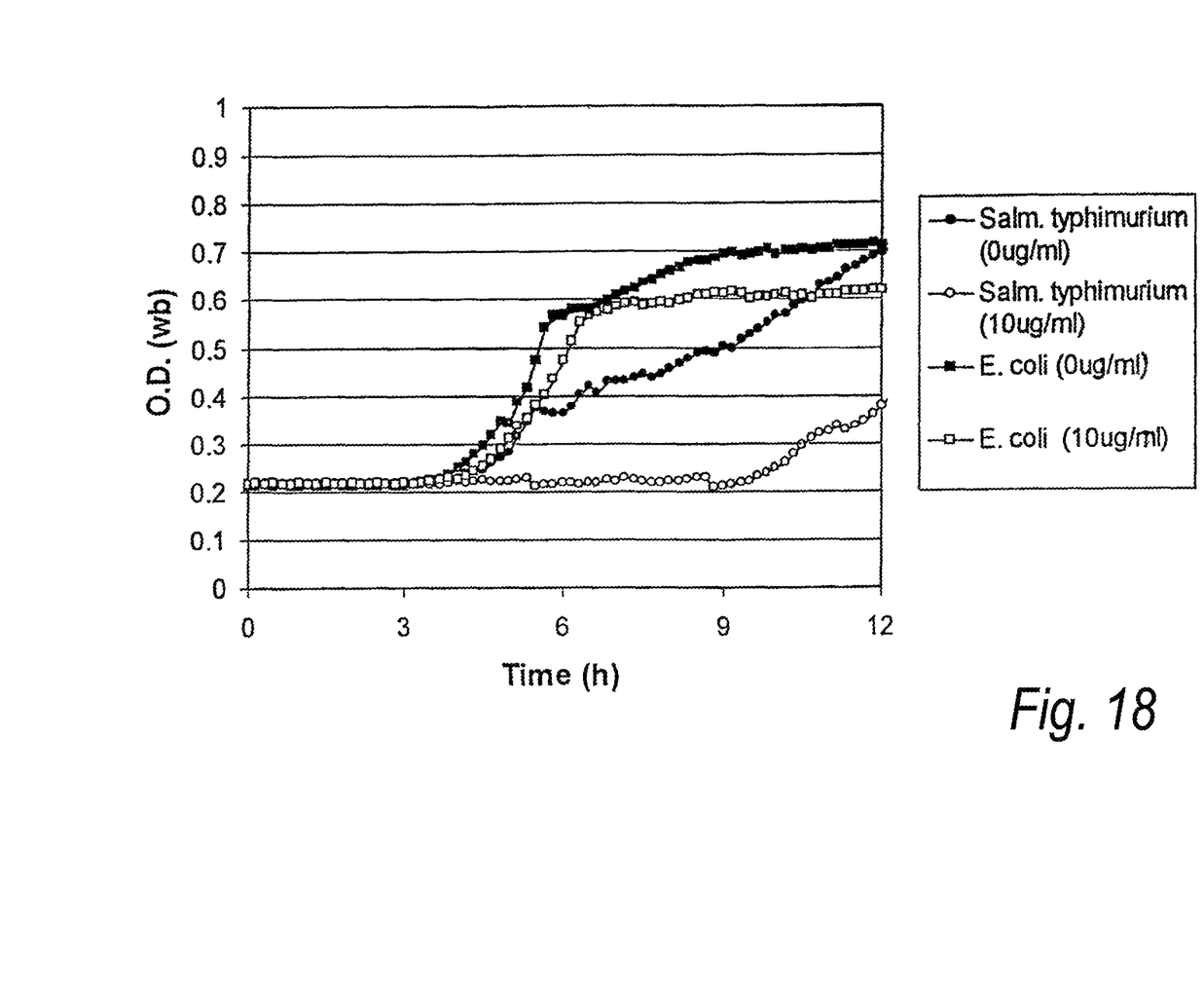
Figure 19:
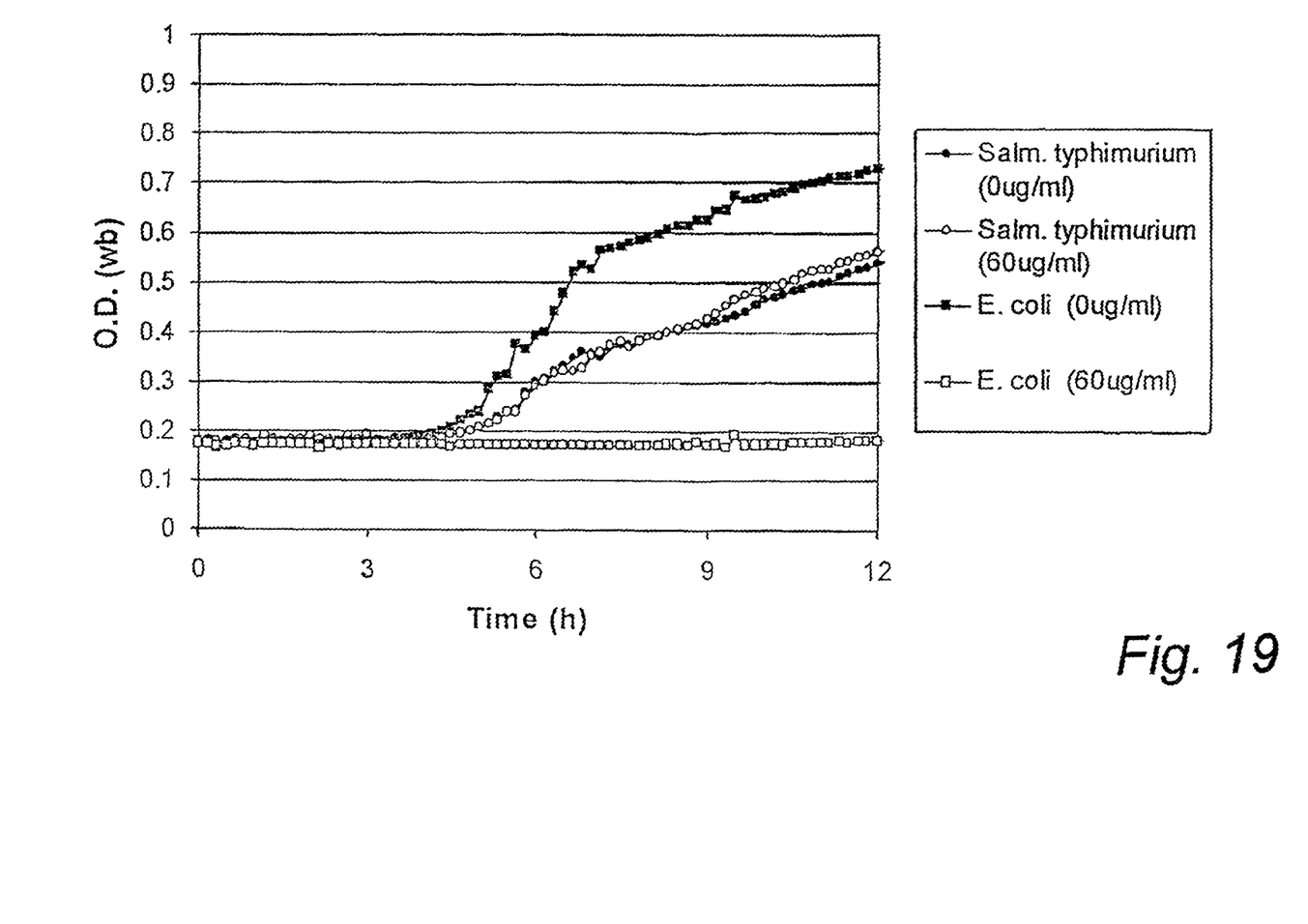

Typical results are shown in FIGS. 17-19, which are graphs of optical density against time for *S. typhimurium* (circles) and *E. coli* (squares) in the presence (empty symbols) or absence (filled symbols) of 15 µg/ml cefsulodin (FIG. 17), 10 µg/ml novobiocin (FIG. 18) or 60 µg/ml alaphosphin (FIG. 19). It is apparent from these results that both cefsulodin and novobiocin significantly inhibit the growth of *S. typhimurium*. Thus, in FIGS. 17 and 18 growth curves of *S. typhimurium* in the presence or absence of these two agents are substantially divergent and, in each case, at 12 hours *E. coli* substantially outgrows *S. typhimurium* in the presence of the selective agent. In contrast, in FIG. 19 it is apparent that there is no significant difference in the growth of *S. typhimurium* in the presence or absence of alaphosphin at 60 µg/ml. Moreover, growth of *E. coli* is completely inhibited, allowing *S. typhimurium* easily to outgrow its competitor.

Example 13

Medium composition was found to affect the inhibition of growth of organisms by pyroglutamyl-1-aminoethylphosphonic acid. In general, media containing a higher concentration of short chain peptides, for example hydrolysed casein, reduced the effectiveness of the inhibitor. Thus, Pyr-AEP was dissolved in deionised water (51.2 mg/ml), filter sterilised, and amounts of the solution added to autoclaved Bacteriological Peptone, Casein Hydrolysate, Lab-Lemco broth and Proteose Peptone (20 g/l; pH 7.3) to give a dilution series of 1,477, 739, 369, 185 µg/ml. Volumes (300 µl) of these solutions were then pipetted into the wells of Bioscreen microtitre plates and 30 µl quantities of 1 in 10,000 dilutions of overnight cultures of *Citrobacter freundii* OCC 261, *Enterobacter aerogenes* OCC 720, *Salmonella enteritidis* OCC 723 and *Salmonella virchow* OCC 703 added. Plates were then covered, incubated at 37° C., and the opacity of the organism suspensions, measured using a Bioscreen instrument. From the resulting growth curves, MIC values were generated as shown in Table 4 below.

TABLE 4

Minimum inhibitory concentrations of L-Pyroglutamyl-1-aminoethylphosphonic acid-aep (µg/ml) in various media

| Strain | Medium | | | |
| --- | --- | --- | --- | --- |
| | Casein Hydrolysate | Bacteriological Peptone | Proteose Peptone | Lab-Lemco |
| *Salmonella enteritidis* OCC 723 | >1343 | 671 | 1343 | 1343 |
| *Salmonella virchow* OCC 703 | >1343 | 671 | 1343 | 1343 |
| *Citrobacter freundii* OCC 261 | >1343 | 168 | 1343 | 168 |
| *Enterobacter aerogenes* OCC 720 | >1343 | 671 | >1343 | 336 |

Example 14

In view of the importance of being able to recover stressed cells, experiments were conducted to investigate if free AEP had any toxic effect on stressed cells.

*Salmonella typhimurium* (OCC 1792) was heat stressed at 51.4° C. for 25 minutes according to the protocol of Stephens et al. (1997 J. Appl. Micro. 83, 445-455). Cells were diluted in 7 different resuscitation media: yeast extract broth with a high reactive oxygen species content that is inhibitory to stressed cells, SPRINT enrichment broth supplemented with Oxyrase that is an optimised resuscitation medium, BPW as the control that has typical resuscitation properties, BPW supplemented with NaCl that is inhibitory to stressed cells, and BPW supplemented with 3 different levels of AEP. Resuscitation was quantified using a microtitre MPN method.

Figure 20:
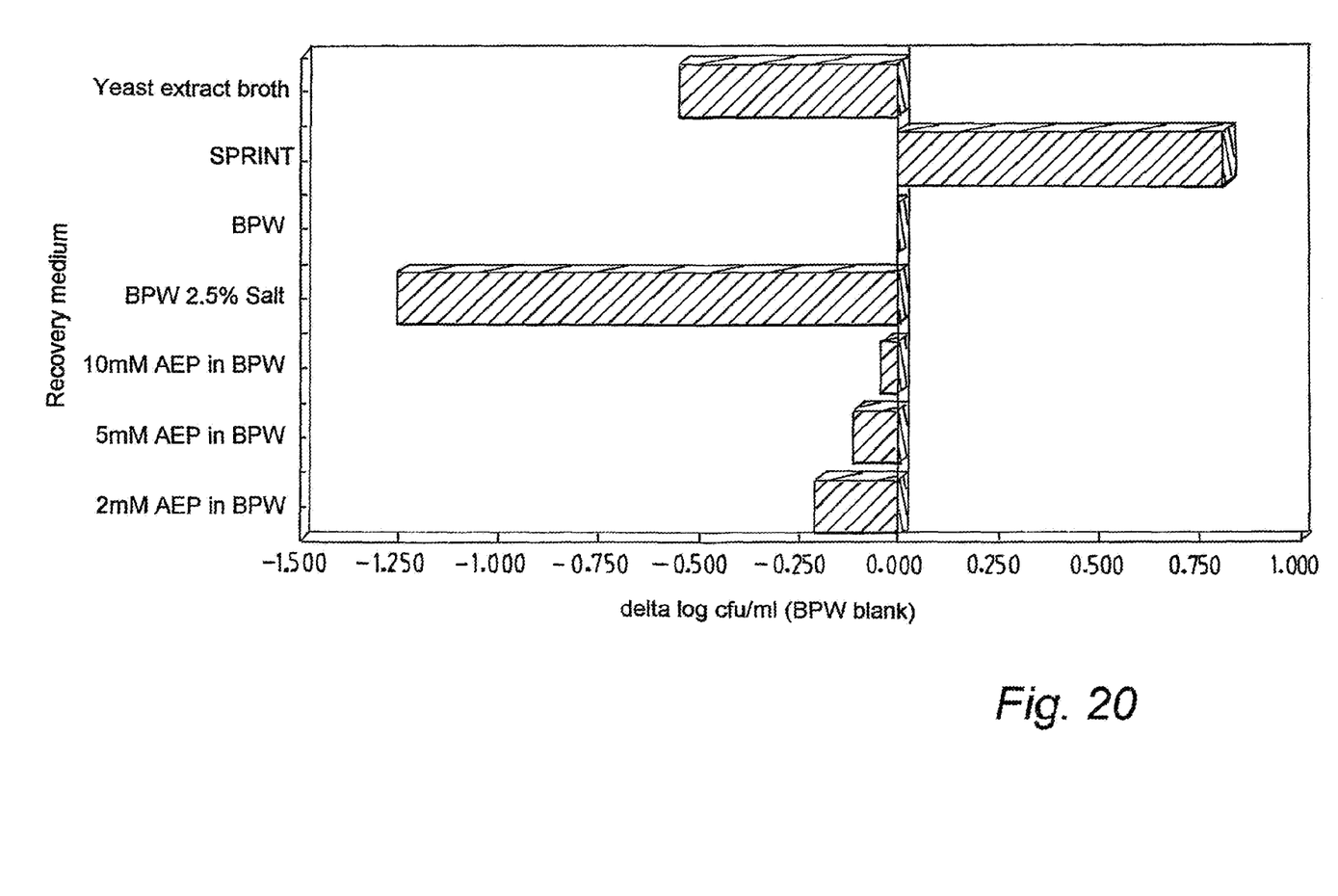
FIG. 20 is a bar chart showing the effect of various media on the recovery of heat-stressed *S. typhimurium* cultures.
Figure 21:
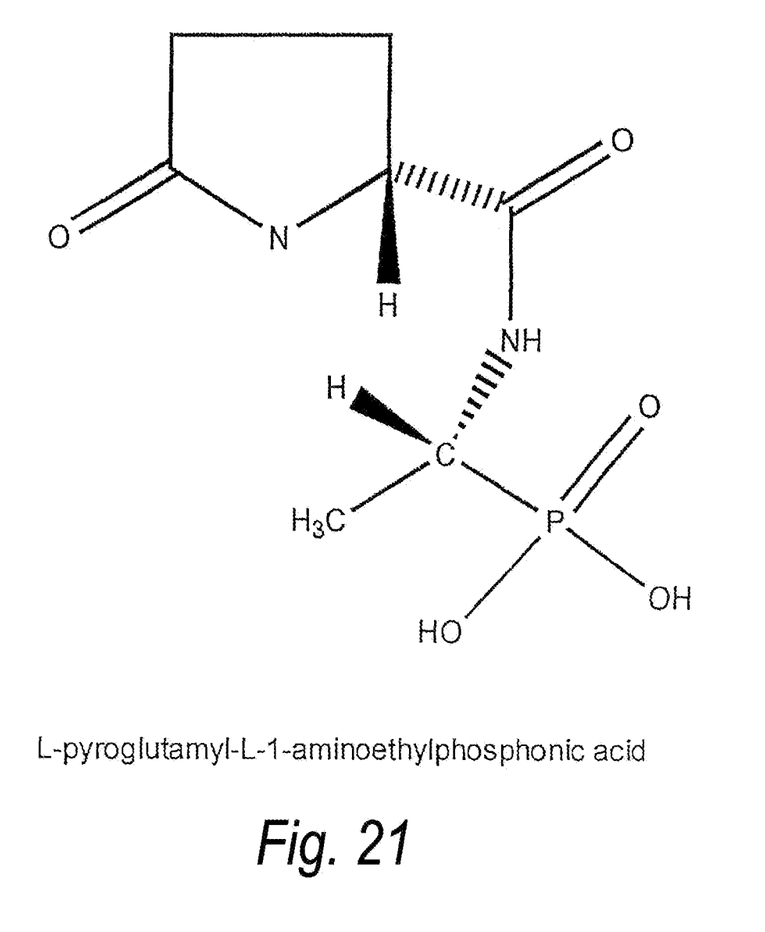
FIG. 21 shows the structure of a particular selective agent (L-pyroglutamyl-L-1-aminoethylphosphonic acid) suitable for use in the method of the invention.

Typical results are shown in FIG. 20 which is a bar chart showing the difference in growth (Log cfu/ml) of the stressed cells in various media relative to growth in BPW alone. The chart shows that the addition of AEP did not significantly affect the resuscitation of heat-stressed *Salmonella* (the variability of the MPN technique being +/−0.25 log).

The invention claimed is:

1. A method of selectively inhibiting the growth of non-target bacteria cells in a mixed population of target and non-target bacteria cells, the method comprising the steps of:
    (a) contacting the mixed population with a growth medium containing a selective agent comprising a carrier moiety linked to a toxic moiety; wherein the carrier moiety comprises an amino acid residue and is linked by a scissile peptide bond linkage to a toxic moiety comprising a 1-aminoalkyl phosphonic acid or a salt thereof; wherein the selective agent is able to enter non-target cells in which the scissile linkage is cleaved, releasing the toxic moiety to exert a toxic effect on the non-target cells causing inhibition of the growth of the non-target cells, whereas the scissile linkage is not cleaved in target cells or the toxic moiety, if released from the selective agent, does not exert a toxic effect on the target cell; and
    (b) culturing the bacteria cells in conditions which allow for growth of target cells.

2. The method of claim 1 wherein the method is performed without contacting the mixed population with a pre-enrichment medium that lacks the selective agent.

3. The method of claim 1 wherein, prior to the culturing step, the number of non-target cells in the mixed population is greater than the number of target cells in the mixed population.

* * * * *